(12) United States Patent
Schnell et al.

(10) Patent No.: US 8,733,359 B2
(45) Date of Patent: May 27, 2014

(54) COLLAR OF A RESPIRATORY DEVICE

(75) Inventors: Ralf Schnell, Seligenstadt (DE); Franz Waldeck, Nieder-Olm (DE)

(73) Assignee: Tracoe Medical GmbH, Frankfurt am Main (DE)

( * ) Notice: Subject to any disclaimer, the term of this patent is extended or adjusted under 35 U.S.C. 154(b) by 1018 days.

(21) Appl. No.: 12/442,125

(22) PCT Filed: Sep. 13, 2007

(86) PCT No.: PCT/EP2007/059609
§ 371 (c)(1),
(2), (4) Date: Jul. 7, 2009

(87) PCT Pub. No.: WO2008/034751
PCT Pub. Date: Mar. 27, 2008

(65) Prior Publication Data
US 2010/0006102 A1  Jan. 14, 2010

(30) Foreign Application Priority Data

Sep. 20, 2006 (DE) .......................... 10 2006 044 740

(51) Int. Cl.
*A61M 16/00* (2006.01)
*A61M 16/04* (2006.01)

(52) U.S. Cl.
CPC ... *A61M 16/0434* (2013.01); *A61M 2016/0456* (2013.01)
USPC .................................. 128/207.15; 128/207.14

(58) Field of Classification Search
USPC ............. 128/207.14–207.16; 604/96.01–104; 606/191–199
See application file for complete search history.

(56) References Cited

U.S. PATENT DOCUMENTS

| | | | |
|---|---|---|---|
| 3,481,339 A | | 12/1969 | Puig |
| 4,248,236 A | * | 2/1981 | Linder ...................... 604/100.01 |
| 4,423,725 A | * | 1/1984 | Baran et al. .............. 128/207.15 |
| 4,791,923 A | | 12/1988 | Shapiro |
| 5,038,777 A | | 8/1991 | Dunn |
| 5,076,268 A | * | 12/1991 | Weber ...................... 128/207.15 |
| 5,201,310 A | | 4/1993 | Turnbull |
| 5,392,774 A | * | 2/1995 | Sato ......................... 128/207.15 |
| 5,447,152 A | | 9/1995 | Kohsai et al. |
| 5,447,497 A | * | 9/1995 | Sogard et al. ............. 604/101.02 |
| 5,512,051 A | * | 4/1996 | Wang et al. .............. 604/103.14 |
| 5,733,316 A | * | 3/1998 | Tierney et al. ................ 607/101 |

(Continued)

FOREIGN PATENT DOCUMENTS

| | | |
|---|---|---|
| DE | 25 38 268 | 3/1977 |
| DE | 198 55 521 A1 | 6/2000 |
| JP | 2005-40277 | 2/2005 |

*Primary Examiner* — Melanie Hand
*Assistant Examiner* — Aundria Hairell
(74) *Attorney, Agent, or Firm* — Paul & Paul

(57) ABSTRACT

The invention concerns a collar with a tracheotomy cannula or tube, wherein the collar embraces a respiratory tube in sealing relationship. The collar comprises separate inner and outer films, the outer film being elastically stretchable. The collar of the device allows no or only small tight folds formed which do not affect sealing integrity between the collar and the trachea wall even at low pressures. The outer film is expandable to a diameter larger than the diameter of a trachea, and in particular is at least 1.5 times the outside diameter of the tube, and the inner film comprises a material of lower elastic stretching. The inner film is produced oversized and without an external restriction at an internal pressure of at most 20 hPa assumes a diameter which is larger than the diameter of a trachea.

24 Claims, 2 Drawing Sheets

(56) References Cited

U.S. PATENT DOCUMENTS

Figure 1:
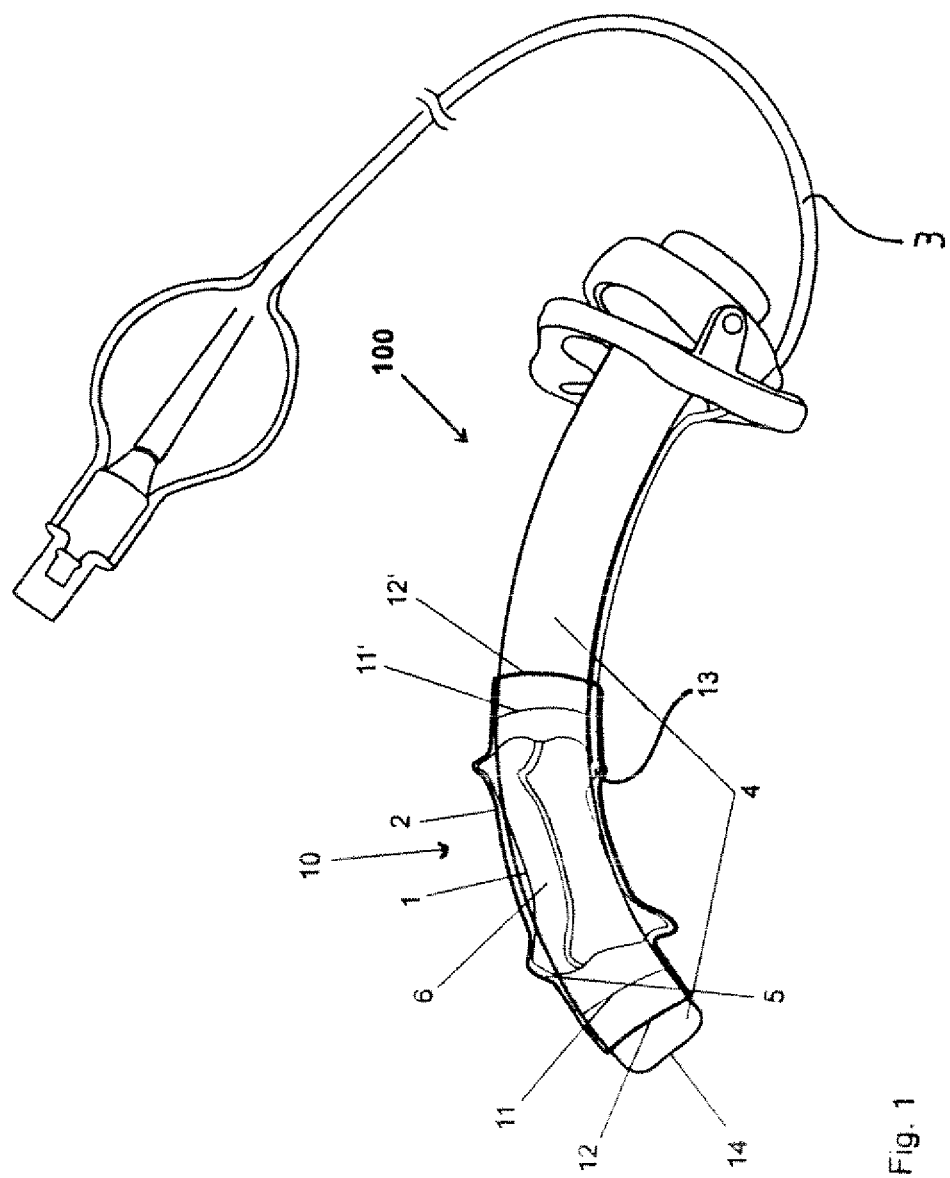

| | | | |
|---|---|---|---|
| 5,868,776 A * | 2/1999 | Wright | 606/194 |
| 6,745,773 B1 | 6/2004 | Gobel | |
| 6,802,317 B2 | 10/2004 | Gobel | |
| 2002/0150707 A1 * | 10/2002 | Wilkins | 428/35.2 |
| 2004/0236365 A1 | 11/2004 | Cioanta et al. | |
| 2005/0284482 A1 | 12/2005 | Patel | |
| 2008/0078403 A1 * | 4/2008 | Clayton | 128/207.15 |
| 2008/0092902 A1 | 4/2008 | Schnell | |
| 2009/0107510 A1 * | 4/2009 | Cornish et al. | 128/207.15 |

* cited by examiner

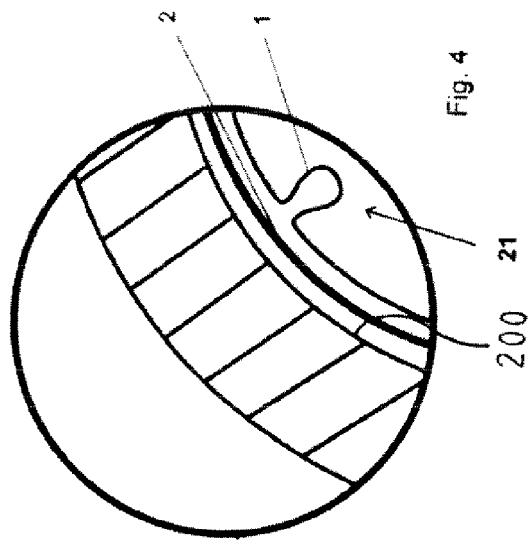
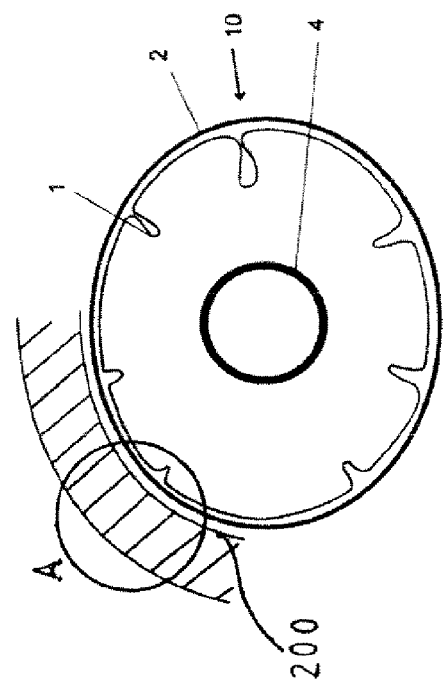
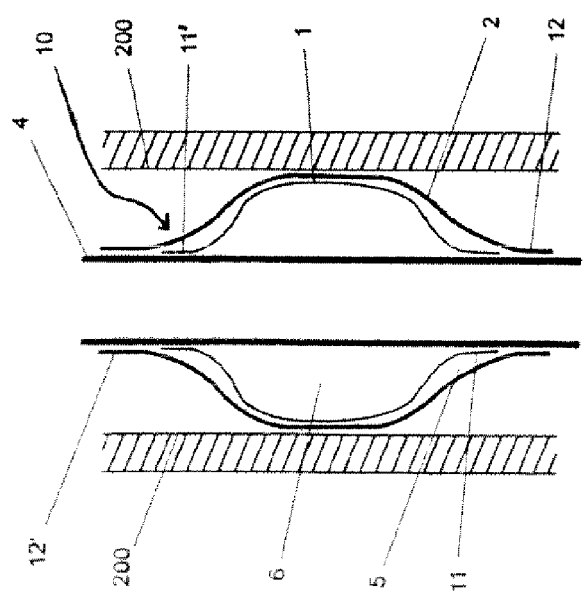

COLLAR OF A RESPIRATORY DEVICE

The present invention concerns the collar of a respiratory device, in particular a tracheotomy cannula or an endotracheal tube, wherein the collar embraces a respiratory tube and is fixed thereto in sealing relationship and the collar comprises an inner film and an outer film, wherein the inner and the outer films are separate from each other and the outer film comprises an elastically easily stretchable material.

Collars in relation to tracheotomy cannulas or endotracheal tubes have long been known. The collars serve on the one hand to fix and center a tube in the trachea of a patient so that lower edges or rims as far as possible do not come into engagement with the wall of a trachea. On the other hand the collar also involves the function, in particular in the case of patients who can no longer themselves actively assist with breathing, of preventing escape of the respiratory air supplied through the tube outwardly by way of the pharyngeal cavity.

It will be noted however that it is known that, particularly in the case of long-term use of such respiratory devices, complications frequently arise, which can be related inter alia to the collar.

As already mentioned the collar is intended on the one hand to prevent respiratory air supplied through the tube from escaping upwardly again past a tube through the pharyngeal cavity, but conversely the collar is also intended to prevent for example secretions, fluid and possibly also food residues which can pass by way of the pharyngeal cavity into the trachea and accumulate above the collar being able to go past the collar and in that way getting into the bronchial tubes and the lungs. In particular secretion which accumulates for a prolonged period above the cuff or the collar can in that case also suffer bacteriological contamination in the course of time so that the fact of such secretions passing the collar or going between the outside wall of the collar and the inside wall of the trachea can not infrequently lead to lung inflammations or other infections.

In principle it would admittedly be possible to achieve a secure seal between the outside wall of a collar and the wall of the trachea if the collar is inflated with a sufficient pressure, but the result of this is that the wall of the trachea is subjected to a pressure which leads to damage and finally necrotisation of the tissue. The attempt is made to prevent that inter alia by the use of collars of an oversize, which comprise a substantially non-stretchable material, in which case the collar which is inflated to a slightly increased pressure of for example 20 hPa assumes, in the restriction-free state, a diameter which is certain to be larger than the diameter of the trachea in which the respiratory device in question is used. Typically the diameters of such collars involving an oversize, in the inflated free state, are in the range of between 20 mm and 35 mm.

As the diameter of a trachea is in each case smaller than the diameter of such a fully inflated collar, the use of such collars has the advantage that, when the collar is inflated under a pressure of for example 20 hPa, it is possible to be sure that the pressure exerted by the collar in turn against the wall of the trachea is also 20 hPa, that low pressure excluding damage to and necrotisation of the tissue.

Even if by virtue of that advantage use of substantially non-elastically stretchable collars involving an oversize has extensively gained acceptance, those collars however suffer from the disadvantage that they necessarily form wrinkles and folds at their outside periphery as they cannot expand to their full volume within the trachea. Those folds in turn have the result that the collar does not bear sealingly against the wall of the trachea everywhere along the entire periphery of the collar. In addition, when folds are turned inwardly, passages can be formed along the folds, through which fluids or secretions which collect above the collar in a trachea can flow past the collar into the bronchial tubes and the lungs. That is discussed in detail for example in DE 198 55 521.

Numerous attempts have therefore already been made to produce and improve the collars in such a way that such fold formation is either minimised or the folds are at least so small and narrow that fluids or secretions cannot pass between the collar and the wall of the trachea at any event to an extent worth mentioning.

It will be noted however that the demands to be made on the collar to attain those properties are in many respects not compatible with each other and also not compatible with the specific conditions of use. If the collar is made from a very soft and ductile material, there is the danger that such a collar already tears upon being introduced into the trachea, particularly if the collar is arranged on a tracheotomy cannula and has to be introduced through a narrow tracheostoma or is damaged in such a way that it can no longer fulfil its function.

In contrast a correspondingly more stable and more tear-resistant material is generally not sufficiently ductile and flexible to be certain of making the folds produced sufficiently small so as to avoid leaks.

The attempt has also already been made to reduce the wall thickness of the material from which such collars are made (for example polyurethane) to an extreme extent, down to values of below 10 μm, for example 5 μm, to achieve that aim. Such thin-wall collars however are also relatively sensitive and difficult in terms of handling, in particular in relation to tracheotomy cannulas. In addition, such thin-wall collars no longer guarantee adequate sealing integrity for the collar wall in relation to water vapor so that water can collect in the collar, whereby the function of the collar is adversely affected.

Further attempts in regard to a better seal involved applying different coatings to the film of the collar, as described for example in DE 198 55 521, or using multi-layer films. In that case the outer layer was to be as hydrophilic or swellable as possible in order to permit absorption of fluid and good contact against the trachea. Such an outer layer can also contain substances which prevent or retard bacterial growth. Even if in part good results were achieved thereby, the fact that the collar does not bear against the trachea without gaps cannot always be completely compensated thereby.

The use of a plurality of collars has in part also been proposed. DE 196 38 935 and DE 198 45 415 propose arranging above the collar (cranially thereof) a tamponing balloon which can be enlarged by a supply of fluid and which has an additional sealing function. That tamponing balloon can also expand caudally and completely enclose the collar. Due to separate filling of the collar and the tamponing balloon, in that arrangement control of the pressure exerted on the trachea wall is possible only with difficulty and a necessary additional fluid system increases the complication in handling.

U.S. No 2004/0236365 discloses a catheter, in particular a urethra catheter, in which an anchorage or treatment balloon is covered by an elastic collar. That collar serves to compress the balloon upon insertion and removal of the catheter and it therefore exerts a strong pressure on the respective balloon. That pressure first has to be overcome when inflating the balloon. It is therefore very difficult with that arrangement to determine the actual pressure loading on the urethra, whereby damage to the tissue can occur in long-term uses.

Therefore the object of the present invention is to provide a corresponding collar and a respiratory device equipped with such a collar, which on the one hand it sufficiently stable and easy to handle but which does not allow any folds or only very small tight folds to be formed, which do not adversely affect the sealing integrity of the engagement between the collar and the wall of the trachea even with low internal pressures in the collar of for example 20 hPa.

That object is attained in that, in a collar comprising an inner film and an outer film separate therefrom, the outer film is expandable at an internal pressure of at most 50 hPa to a diameter which is larger than the diameter of a trachea for which the respiratory device is intended, and in particular is at least 1.5 times the outside diameter of the tube, and the inner film comprises a material of lower elastic stretching, wherein the inner film is produced with oversize and without an external restriction at an internal pressure of at most 20 hPa assumes a diameter which is larger than the diameter of a trachea for which the collar is intended.

In that case the outer film is to comprise an elastically easily stretchable material while the inner film comprises a material involving lesser elastic stretching. In that respect the term 'elastically easily stretchable material' is used to denote a material which for example under an internal pressure of a closed balloon comprising such a material of between 10 hPa and 15 hPa stretches by at least 20%, preferably at least 50% or more.

In contrast thereto the inner film can admittedly possibly also be elastically stretchable, but at any event it is produced with an oversize so that in any case it cannot assume a stretched condition within the restricting dimension of a trachea and preferably stretches by less than 10%, in particular by less than 1% for example at a pressure of between 15 hPa and 20 hPa. The feature whereby the inner collar is produced with an oversize and without external restriction at an internal pressure of at most 20 hPa assumes a diameter which is larger than the diameter of a trachea for which the collar is intended is intended to express the fact that the diameter of the film or the inner collar, when the collar is filled without external limitation so that the film is fold-free, is larger than the inside diameter of the trachea for which the collar is intended. In the case of a tracheal cannula for adults the inside diameter of the trachea is approximately double the outside diameter of the tube. Tracheal cannulas for children generally have a tube of a relatively large outside diameter in comparison with the inside diameter of the trachea. Collars produced with an oversize are known in the state of the art and are also referred to as 'high-volume-low-pressure collars'. It will be appreciated that, for inflating such a collar, a slightly increased pressure of 1-2 hPa can already be sufficient while however in practice an increased pressure of about 20 hPa is used to inflate such a collar in the trachea.

In contrast in a preferred embodiment of the invention the outer film should elastically expand to a diameter which is larger than the diameter of a trachea for which the collar is intended and which in particular is at least double the outside diameter of the cannula or the tube, at an internal pressure of at most 50 hPa, preferably at most 30 hPa and particularly preferably between 5 hPa and 30 hPa.

Such easily stretchable elastic materials cannot in practice be used as the sole collar material as more specifically in such a situation it is not clear as to the direction in which stretching of the collar material overall takes place, that is to say the collar does not unconditionally expand solely in its diameter to such an extent that it sealingly contacts the wall of the trachea, but it can for example also correspondingly expand in the axial direction so that, when solely using such a collar material, that would not guarantee contact against the wall of the trachea along the entire periphery. In addition such an elastically stretchable collar, considered on its own, does not have an adequate centering function and under some circumstances could cover over the opening of the tracheal cannula or the tube.

The use of a substantially non-stretchable inner collar or inner film provides however that it almost exclusively radially expands in a defined fashion by virtue of its predetermined shape and in so doing also stretches the easily elastically stretchable outer film substantially only in the radial direction. The folds forming in that case on the outside of the inner film are then readily bridged over by the elastically stretchable material of the outer film which consequently assumes an ideal shape in respect of an envelope for the inner film and thus bears smoothly and in sealing relationship practically along its entire periphery against the wall of the trachea.

As the pressure required for stretching of the outer film to put it into such a condition is known, it is only necessary to increase the pressure of the inner collar by a corresponding amount in order to ensure that the outer wall or film of the collar in turn bears with a pressure of between about 15 hPa and 20 hPa or somewhat less against the wall of the trachea. By way of example, if between 5 hPa and 10 hPa are sufficient to increase the diameter of the outer, elastically stretchable film to two and a half times, it is possible to adjust the internal pressure of the inner collar to between about 20 hPa and 30 hPa so that, after overcoming the inwardly directed elastic force of the outer collar, a residual pressure of about 20 hPa is still transmitted to the wall of the trachea.

A further advantage of the collar which is made up of an inner collar involving an oversize and which is enclosed by an outer, easily elastically stretchable collar is that, even in the event of damage to the outer film, the inner collar acts like a conventional collar and in that way sealing integrity is basically still ensured.

In a preferred embodiment a gas cushion is provided between the inner film and the outer film. It will be noted that that gas cushion can be very small. It prevents the outer film being adapted in respect of its shape to the inner film and possibly 'sticking' to the inner film, whereby once again folds could occur.

Particularly preferably, that gas cushion is completely outwardly delimited and closed off by the inner film and the outer film and optionally the outside wall of the cannula so that the volume of the gas cushion does not change. When the inner balloon is filled that ensures that the pressure required for stretching the outer film is not altered by fluctuations in the gas volume. That makes it possible to precisely specify the internal pressure of the inner collar to attain a given pressure (for example 20 hPa) against the wall of the trachea. The gas is in that respect also not significantly compressed as it is in an at least partially easily stretchable space.

Preferably the volume of the gas cushion is less than 20% of the volume of the inner collar in the freely filled condition, that is to say when filling the collar without external limitations until the inner film is fold-free. In that respect the term 'inner collar' is used to denote the collar which is formed exclusively by the inner film and which is arranged around the respiratory tube. The expression 'filling the collar' is thus used to mean filling the inner collar. The gas cushion is to be of a small volume as the spacing between the inner and outer films both in the unfilled condition of the collar is to be small in order to permit easy introduction and also in the filled condition, thereby providing for stabilisation of the outer film by the inner film.

It is further preferred if disposed between the inner and outer films is a substance which prevents the films from clinging to each other. Such a substance can be for example talcum or a lubricating fluid or lubricant gel (for example KY-Jelly). That substance can be provided in addition to a gas cushion or instead of a gas cushion between the inner and outer films. It ensures that the two films remain movable relative to each other and the outer film thereby encompasses the inner film in particular in the inflated condition with a small external surface. Otherwise however the material of the two films can also be so selected that they deploy only very slight adhesion forces so that they are practically excluded from adhering to each other.

In a particularly preferred embodiment the outer and the inner films are of different moduli of elasticity and/or Shore hardnesses, wherein the inner and the outer films can basically be produced from the same material insofar as chemically identical materials can be readily produced in different hardnesses and of different elasticities, as applies for example to polyurethane or other thermoplastic elastomers, in particular copolymers. Further examples of such materials are thermoplastic elastomers. Those materials generally contain hard and soft segments. The modulus of elasticity or the Shore hardness of the material can be adjusted over wide ranges by a variation in the relationship of soft to hard segments and by the content and the nature of the crosslinkings.

In addition however it is also preferable to select for the inner and the outer films different materials which are advantageous in particular for achieving easy stretchability with a low level of tension in the outer film and the stability of the inner film. In that respect the only important consideration is that both the inner and the outer films, at their upper and lower ends respectively, can each be fixedly and sealingly connected to the tube or also to each other.

Preferably the inner film comprises one of the materials polyurethane, polypropylene, polyethylene, polyethylene terephthalate, polyvinyl chloride or other polymers and mixtures of polymers (blends) and the outer film comprises at least one of the polymers polyurethane. SEBS (styrene-ethene-butene-styrene), SBS (styrene-butadiene-styrene), SIS (styrene-isoprene-styrene), IR (polyisoprene) or other thermoplastic elastomers, latex, silicone, natural rubber or synthetic rubber. In that respect the term thermoplastic elastomers is used to denote materials which have the elasticity, softness and toughness of a thermosetting rubber and the workability of a thermoplastic polymer. They include inter alia styrene block copolymers, polyolefin mixtures, elastomeric alloys, thermoplastic polyurethanes, thermoplastic copolyesters and thermoplastic polyamides as well as mixtures (blends) thereof. Further materials are also conceivable, including those which are possibly still being developed and which have the desired properties in respect of the outer or inner film. It will be appreciated that the materials of the inner and in particular the outer film are biocompatible or body-compatible, that is to say they are not damaged by and they also do not damage the environment within the body and in particular within the trachea. In particular synthetic latex or rubber which is free of allergens can be used.

At least one of the films should be a water vapor-impermeable film, in which respect it is preferred if the outer film is water vapor-impermeable so that no water can penetrate into the intermediate space between the outer and inner films. The inner film can be water vapor-impermeable so that, in the event of damage to the outer film, it can perform at least a limited sealing function.

If the collar, that is to say the cavity which is between the inner film and the respiratory tube, is filled with a fluid, at least the inner film must be water vapor-impermeable in order to prevent fluid or water vapor from passing through into the gas cushion between the inner and outer films.

Desirably both films are also connected together firmly and in sealed relationship at least along a portion which is connected firmly and in sealed relationship to the tube, in which respect however it would also be fundamentally possible for the outer film to be connected to the tube axially above and below the portions, along which the inner film is connected to the tube. In that case the inner film should be delimited completely by the outer film in relation to the lumen of the trachea.

In a further embodiment of the invention the inner and/or the outer film can be coated. In that case a coating is a thin layer which is not self-supporting. That coating can be on the outer film for example an outwardly directed hydrophobic or hydrophilic layer. Such a coating can also contain bactericidal or bacteriostatic substances. For example a coating containing silver or silver compounds would be possible. A coating which prevents the films from clinging together can also be appropriate, on the film surfaces which bear against each other.

Preferably the inner and/or the outer film respectively comprise a plurality of film layers which are fixedly connected together. In particular the outer film which on the one hand is to be elastically easily stretchable and which on the other hand is to afford as much sealing integrity as possible in relation to water vapor and water can achieve those properties by two different film materials which are joined together, in the form of thin film layers. If the film layers comprise different materials which are difficult to join together, what is referred to as a compatibility procurement agent can be used for joining the film layers. Such compatibility procurement agents are for example copolymers, in particular diblock copolymers. If the materials to be used permit it, the film layers of the individual films of the collar can also be co-extruded with each other or laminated on to each other.

Desirably the wall thickness of the inner film is between 20 µm and 100 µm, preferably between 50 µm and 100 µm. That wall thickness range permits adequate stabilisation of the outer film with at the same time adequate flexibility and adaptability of the inner film, the size of the folds which are formed in the inner film playing no part as they are bridged over by the outer film.

The wall thickness of the outer film in the pressure-less condition is desirably between 20 µm and 600 µm, preferably between 50 µm and 400 µm and particularly preferably between 100 µm and 300 µm. The outer film is loaded by shearing forces in particular upon introduction of the cannula or the tube and must therefore be of an adequate wall thickness to withstand that mechanical loading. On the other hand the film must be sufficiently elastically stretchable to not afford a high level of resistance upon filling of the collar and to ensure optimum adaptation to the wall of the trachea.

A preferred embodiment of a collar or a respiratory device having a tube is characterised in that the outer and inner foils are of substantially the same axial length and extend substantially over the same axial region of the tube, wherein outer and inner films are respectively fixed in sealed relationship at the same axial positions to the tube or to each other. That contributes to no or only a very small intermediate space remaining between the outer and inner films, and that prevents parts of the highly elastic outer film being displaced with respect to the inner film to a significant degree.

Further advantages, features and possible uses of the present invention will be clearly apparent from the description hereinafter of a preferred embodiment and the accompanying Figures in which:

FIG. 1 shows a diagrammatic view of a tracheotomy cannula with an embodiment of a collar according to the invention, FIG. 2 shows a view in longitudinal section of a windpipe (trachea) with a tracheotomy cannula with an embodiment of a collar according to the invention in the filled condition, FIG. 3 shows a cross-section through a respiratory tube with a collar according to the invention which bears against a trachea wall which is only indicated, and FIG. 4 shows a section on an enlarged scale through the collar bearing against the trachea wall, corresponding to the circle A in FIG. 3.

FIG. 1 shows a tracheal cannula 100 with a collar 10 in a partially inflated condition. When the inner and outer film bear closely against the tube by emptying of the inner collar the tracheal cannula can be introduced into the trachea. The collar 10 of that cannula comprises an inner film 1 which is connected to the respiratory tube 4 of the tracheal cannula 100 at the connecting locations 11 and 11' and an outer film 2 which is connected to the respiratory tube 4 at the connecting locations 12 and 12'. The connecting locations 11, 11', 12 and 12' are each such that they are air- and gas-impermeable.

The inner film 1 corresponds to what is referred to as a 'high-volume-low-pressure collar' which is produced with an oversize and which in the completely deployed filled condition is of a larger diameter perpendicularly to the respiratory tube 4 than the diameter of the trachea, for which the collar is intended. The outer film 2 comprises an elastically very easily stretchable material, it is stretchable at a very low internal pressure of less than 30 hPa to a diameter which is larger than the diameter of a trachea, for which the collar is intended. By virtue of the very easy stretchability, the outer film 2 alone could not be used as what is referred to as a 'low-volume, high-pressure collar' as it is of excessively low stability in respect of shape and as a result could possibly close up the opening 14 of the respiratory tube 4 upon being filled.

The inner collar is produced from materials which are usual for 'high-volume, low-pressure collars'. The outer collar comprises SIS, SBS, SEBS, other thermoplastic elastomers or a mixture thereof which can be obtained with the desired properties for example from Kraton. With a wall thickness for the outer collar of for example between 100 μm and 300 μm the above-mentioned materials can be readily so adjusted, for example for SBS in terms of the ratio of styrene to butadiene, that a collar produced therefrom, at a pressure of between 5 hPa and 30 hPa, is at least doubled in its diameter in relation to the pressure-less condition, or expands to a diameter which corresponds at least to double the diameter of the tube.

Disposed between the inner and outer collars is a small amount of gas 5, for example air or also $CO_2$ or $N_2$, which serves to keep the two films separate, the volume of which however is so small that the outer film 2, in the emptied condition of the inner collar, closely embraces the respiratory tube 4 and the inner film 1. Optionally instead of the gas use is made of a lubricant gel or a mixture of gas and lubricant gel.

FIG. 1 clearly shows the hose 3 which permits the feed of a fluid, for example air, into the cavity 6 closed off by the inner film 1 and the respiratory tube 4. In that case the fluid passes through the opening 13 into the cavity 6.

FIG. 2 diagrammatically shows a section through a trachea in which there is a respiratory tube 4 with a collar 10. The collar 10, or the cavity 6 between the inner film 1 and the respiratory tube 4, is filled with a fluid. That causes the inner collar to be expanded to such an extent that it would form the largest possible contact surface with the trachea wall 200.

Between the inner film 1 and the trachea wall 200 is the outer film 2 which was stretched by filling of the collar. The outer film 2 bears in a fold-free condition against the trachea wall 200 and in that way bridges over the folds formed by the inner film 1.

Between the inner film 1 and the outer film 2 as well as the respiratory tube 4 is a gas cushion 5 which is sealed off by the connecting locations 11, 11', 12 and 12' of the two films to the respiratory tube. The volume of that gas cushion therefore remains practically unchanged upon filling of the collar. That cushion permits an almost fold-free surface for the outer film in the non-filled condition of the collar. Upon filling, that cushion prevents the inner film and the outer film from adhering to each other, which ultimately leads to the outer film 2 of the collar 10 bearing against the trachea wall 200 in a fold-free condition.

FIG. 3 diagrammatically shows a cross-section through a respiratory tube 4 in the region of the collar 10. The collar is filled in that condition so that it serves for fixing the tracheotomy cannula or the endotracheal tube. The inner collar is filled and the filling pressure is so adjusted that, having regard to the inwardly directed return force of the outer collar (film), the entire collar 10 bears against the trachea wall 200 under a pressure of about 20 hPa. By virtue of the collar 10 being spatially restricted by the trachea wall 200, folds are formed in the inner film 1, which however are bridged over by the outer film 2 which is in smooth contact, so that the overall collar 10 bears smoothly against the trachea wall.

The portion A shown in FIG. 3 is illustrated on an enlarged scale in FIG. 4 to clearly show the contact between the trachea wall 200 and the collar 10. When the collar is in the filled condition within the trachea folds 21 are formed in the inner film 1. In that case the inner collar tensions the outer collar which is formed by the film 2. As a result the outer collar bears in a fold-free condition against the trachea wall 200 and by virtue of its elasticity can also adapt to possible unevenness in the trachea wall. The easy elastic stretchability of the outer collar which itself is not additionally filled means that the pressure exerted on the trachea wall 200 by the overall collar 10 is adjusted by means of the filling of the inner collar.

For the purposes of the original disclosure it is pointed out that all features as can be seen by a man skilled in the art from the present description, the drawings and the claims, even if they are described in specific terms only in connection with certain other features, can be combined both individually and also in any combinations with others of the features or groups of features disclosed here insofar as that has not been expressly excluded or technical aspects make such combinations impossible or meaningless. A comprehensive explicit representation of all conceivable combinations of features is dispensed with here only for the sake of brevity and readability of the description.

The invention claimed is:

1. A collar (10) of a respiratory device, for use in sealing the respiratory device against the wall of a trachea, wherein the collar (10) embraces a respiratory tube and is fixed thereto in sealing relationship and the collar comprises an inner film (1) and an outer film (2), wherein the inner and the outer films are separate from each other and are of different levels of stretchable elasticity; wherein the stretchable elasticity of the outer film comprises an elastically easily stretchable material and comprises means for bridging over any folds in the inner film when the inner and outer films are under internal pressure with the collar sealed against the trachea, characterised in that the stretchable elasticity of the outer film is expandable at an internal pressure of at most 50 hPa to a diameter which is larger than the diameter of a trachea for which the respiratory device is intended, and wherein the stretchable elasticity of the inner film comprises a material of lower stretchable elasticity than the material of the outer film; wherein the stretchable elasticity of the inner film is characterized such that without an external restriction and at an internal pressure of at most 20 hPa it assumes a diameter which is larger than the diameter of a trachea for which the collar is intended.

2. The collar of claim 1, wherein the outer film is expandable at an internal pressure of at most 50 hPa to a diameter at least 1.5 times the outside diameter of the tube.

3. The collar of claim 1, wherein the respiratory device is a tracheotomy cannula.

4. The collar of claim 1, wherein the respiratory device is an endotracheal tube.

5. A collar as set forth in claim 1 characterised in that a gas cushion (5) is provided between the inner film (1) and the outer film (2).

6. A collar as set forth in claim 5 characterised in that the gas cushion (5) is a region which is closed off outwardly between the outer and the inner films.

7. A collar as set forth in claim 5 characterised in that the volume of the gas cushion (5) represents less than 20% of the volume of the inner collar in the freely filled condition.

8. The collar of claim 7, wherein the volume of the gas cushion is less than one ml.

9. A collar as set forth in one of the preceding claim 5 characterised in that a substance, which prevents the two films from adhering to each other, is introduced between the inner film (1) and the outer film (2).

10. The collar of claim 9, wherein the substance between the inner film and the outer film is a lubricant gel.

11. A collar as set forth in one of the preceding claim 5 characterised in that the inner film (1) and the outer film (2) have different moduli of elasticity and/or Shore hardnesses.

12. A collar as set forth in one of the preceding claim 5 characterised in that the inner film (1) and the outer film (2) comprise different materials.

13. A collar as set forth in one of the preceding claim 5 characterised in that the inner film (1) comprises one of the materials polyurethane, polypropylene, polyethylene, polyethylene terephthalate, polyvinyl chloride or other polymers and mixtures of polymers and the outer film (2) comprises at least one of the polymers polyurethane, SEBS (styrene-ethene-butene-styrene), SBS (styrene-butadiene-styrene), SIS (styrene-isoprene-styrene), IR (polyisoprene) or other thermoplastic elastomers, latex, silicone, natural rubber or synthetic rubber.

14. A collar as set forth in one of the preceding claim 5 characterised in that the outer film (2) and/or the inner film (1) is a water vapor-impermeable film.

15. A collar as set forth in one of the preceding claim 5 characterised in that at least along a portion (11, 12, 11', 12') which is fixedly and sealingly connected to the tube (4) both films are in turn fixedly and sealingly connected together.

16. A collar as set forth in one of the preceding claim 5 characterised in that the outer film (2) and/or the inner film (1) is provided with a coating.

17. A collar as set forth in one of the preceding claim 5 characterised in that the outer film (2) and/or the inner film (1) comprise a plurality of film layers which are fixedly connected together.

18. A collar as set forth in one of the preceding claim 5 characterised in that the wall thickness of the inner film (1) is a wall thickness of between 20 μm and 100 μm.

19. The collar of claim 18, wherein the wall thickness of the inner film is between 50 μm and 100 μm.

20. A collar as set forth in one of the preceding claim 5 characterised in that the wall thickness of the outer film (2) is between 20 μm and 600 μm.

21. The collar of claim 20, wherein the wall thickness of the outer film is between 100 μm and 300 μm.

22. The collar of claim 20, wherein the wall thickness of the outer film is between 50 μm and 400 μm.

23. A collar as set forth in one of the preceding claim 5 characterised in that the outer film (2) and the inner film (1) extend substantially over the same axial region, wherein the outer and the inner films are jointly fixed in sealed relationship at the same axial positions to a tube and to each other respectively.

24. An endotracheal or tracheotomy tube characterised in that it has a collar as set forth in one of claims 1 through 5.

* * * * *